United States Patent [19]

Ashley et al.

[11] Patent Number: 4,782,942
[45] Date of Patent: Nov. 8, 1988

[54] CONTAINER FOR A NUMBER OF PACKAGED CONTACT LENSES

[75] Inventors: Charles R. Ashley, Pattenburg, N.J.; Crossman:Russell J., Jacksonville, Fla.; John P. Hennessy, Jacksonville, Fla.; William J. Lahm, Jacksonville, Fla.

[73] Assignee: Vistakon, Inc., Jacksonville, Fla.

[21] Appl. No.: 11,820

[22] Filed: Feb. 6, 1987

[51] Int. Cl.$^4$ ............................................. A45C 11/04
[52] U.S. Cl. ......................... 206/5.1; 206/438; 206/439; 206/1.5; 220/22.3; 422/297; 422/300
[58] Field of Search ................. 206/1.5, 5.1, 363, 370, 206/438, 439, 561, 807; 220/22.3, 374; 422/297, 300, 302, 311

[56] References Cited

U.S. PATENT DOCUMENTS

| | | | |
|---|---|---|---|
| 1,945,773 | 2/1934 | Denneklein | 206/561 |
| 2,851,188 | 9/1958 | Pavelle | 206/561 |
| 3,030,163 | 4/1962 | Gottsegen | 206/509 |
| 3,380,573 | 4/1968 | Gulotta | 206/370 |
| 3,410,391 | 11/1968 | Kanter | 206/1.5 |
| 4,135,868 | 1/1979 | Schainholz | 422/300 |
| 4,219,116 | 8/1980 | Borkan | 206/1.5 |
| 4,363,403 | 12/1982 | Raucci, Jr. et al. | 206/1.5 |
| 4,366,915 | 1/1983 | Seidler | 206/1.5 |
| 4,407,411 | 10/1983 | Lowry | 206/561 |
| 4,493,433 | 1/1985 | Sideri et al. | 206/1.5 |
| 4,541,992 | 9/1985 | Jerge et al. | 422/300 |
| 4,577,773 | 3/1986 | Bitel | 206/561 |
| 4,643,303 | 2/1987 | Arp et al. | 206/438 |
| 4,671,408 | 6/1987 | Raines et al. | 206/1.5 |
| 4,691,820 | 9/1987 | Martinez | 206/5.1 |

FOREIGN PATENT DOCUMENTS 2730895  1/1979  Fed. Rep. of Germany ...... 206/439

OTHER PUBLICATIONS

Packaging Engineer, vol. 28, #, Jan. 1983.

*Primary Examiner*—David T. Fidei
*Attorney, Agent, or Firm*—Donal B. Tobin

[57] ABSTRACT

A container for a number of sealed packages for individual contact lenses. The individual lenses are packed in a sealed container in water and must be steam sterilized. Each individual package is stacked in the container of this invention during sterilization and drains are provided in the container for excess water resulting from the sterilization process. When sterilization is completed the container may be closed and sealed. The container has tamper resistant and tamper evident features.

15 Claims, 3 Drawing Sheets

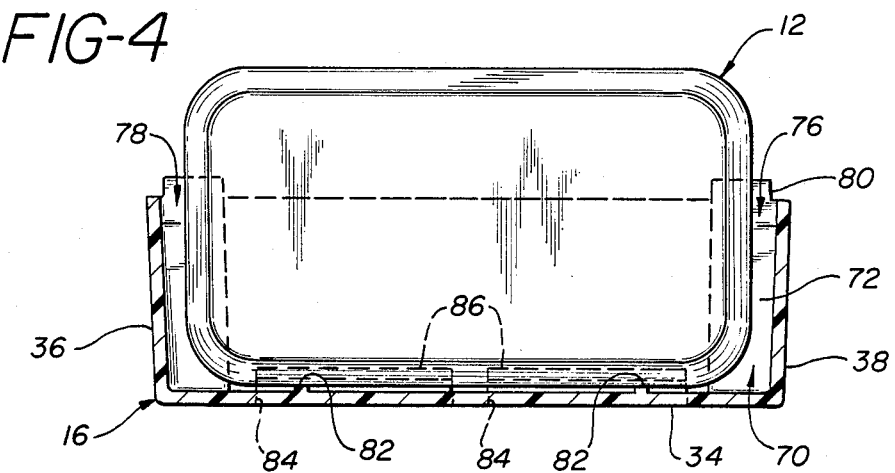
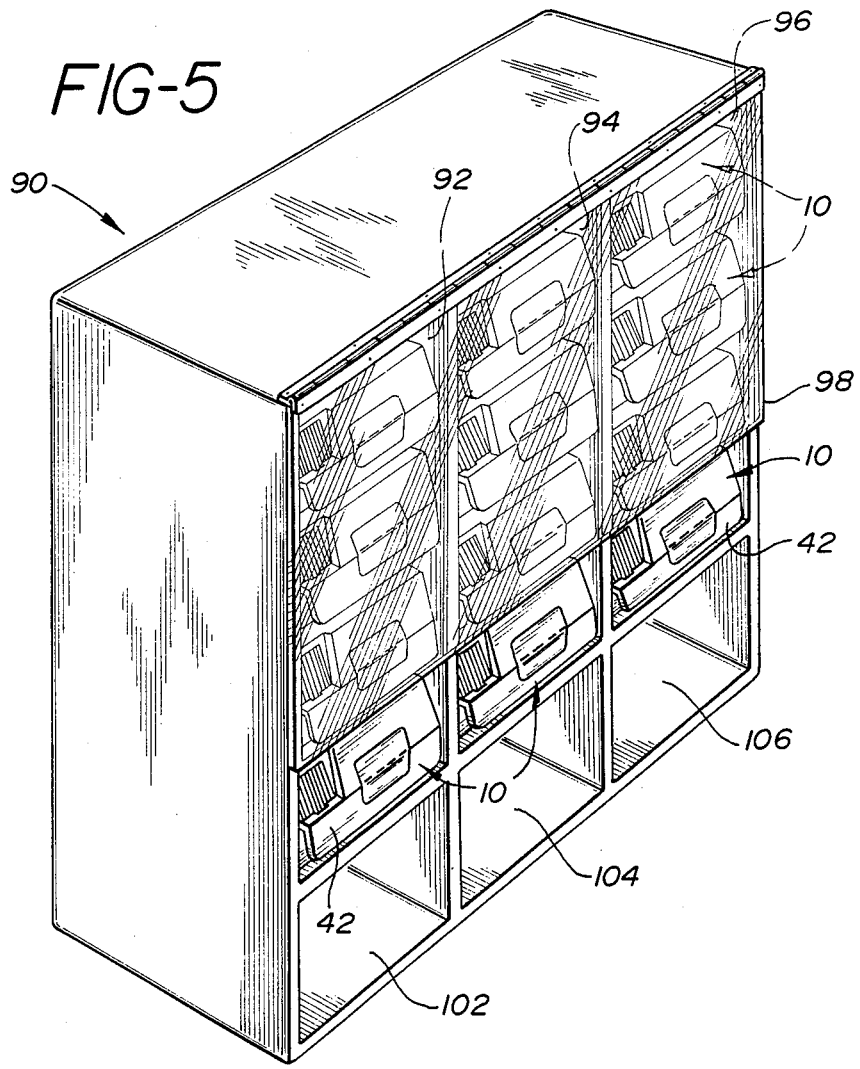

4,782,942

CONTAINER FOR A NUMBER OF PACKAGED CONTACT LENSES

FIELD OF THE INVENTION

The present invention relates to a container for a number of packaged contact lenses, and more particularly, to a container which can hold the individually packaged contact lenses during steam sterilization and which can also function as a container to hold the individually packaged contact lenses during shipment and storage. The container has tamper resistant and tamper evident features.

BACKGROUND OF THE INVENTION

In the past soft contact lenses have been packaged in sterile water or saline solution usually in glass bottles with rubber stoppers and foil seals to hold the stoppers in place on the bottle. Such bottled contact lenses can be easily sterilized because the bottles can be stacked in an autoclave. It is not recommended to sterilize soft contact lenses with radiation because the radiation energy affects the material from which the soft contact lenses are made.

A new package for a soft contact lens is shown in U.S. Pat. No. 4,691,820 and assigned to the Assignee of the present invention. This new package has a plastic base with a recess for holding a soft lens in saline solution. The package is sealed with a removable liquid impermeable laminated sheet. It would be desirable to have a container which could be used to hold a number of individually packaged contact lenses during sterilization then to merely close the container after sterilization and use the same container for shipping and storage of the individually packaged contact lenses. It would also be desirable to have a container which is tamper resistant and which shows evidence of attempts to tamper.

It is also desirable to hold the above-mentioned individual packages for contact lenses while they are being sterilized so that the plastic package does not warp. The warping does not present a serious functional problem, but a warped package would be undesirable from an aesthetic point of view.

SUMMARY OF THE INVENTION

The present invention provides a container for a number of individually packaged contact lenses. The container may be used to hold the individual packages during sterilization and may later be closed and act as a storage and shipping container for the individually packaged contact lenses. Each container includes a bottom portion which has a bottom surface, left and right side walls and front and back side walls all molded integrally together of a suitable plastic. The container also includes a top portion which has a top surface, left and right side walls and front and back side walls all integrally molded together of a suitable plastic. The top and bottom portions are hinged together with an integral hinge to allow the top portion to rotate from an open position into a closed position to form a closed container. The bottom portion of the container includes a series of projections extending from the bottom surface of the bottom portion, integrally formed with said side walls and spaced apart convenient distances along the respective side walls. Each projection is spaced from its neighboring projection a convenient distance to provide a slot for holding the individual packages. Slots on the respective left and right side walls are aligned to hold the individual packages.

The bottom surface of the bottom portion may be provided with a series of small steps aligned with the slots between the upstanding projections to elevate the individual packages above the bottom surface of the bottom portion to permit circulation of sterilizing steam.

Each of the top and bottom portions include drain slots to permit easy circulation of sterilizing steam during sterilization and to permit condensed steam to drain from the container after sterilization.

A latching mechanism is provided to hold the top and bottom portions together in a closed position.

An extension from the front wall of the bottom portion extends along a major portion of the bottom portion front wall and defines an edge. A skirt projects downwardly from the edge to provide a draw pull for easily handling the container.

The container has a number of tamper resistant features. An upstanding ridge extends along the extension behind the seam formed between the top and bottom portion front walls when the top portion closes on the bottom portion. This upstanding ridge prevents the insertion of a sharp object which could tamper with the individual packages inside the container. The projections along the left and right side walls of the bottom portion extend above the top surface of the bottom portion side walls to provide an impediment to the insertion of a sharp object from the side of the container when the top portion is closed upon the bottom portion of the container.

There are L-shaped baffles covering the drain slots to inhibit the insertion of an instrument that could tamper with the contents. A label extends across the top portion front wall and the bottom portion front wall to provide evidence of a chance to open the package. One would have to tear the label in order to open the package.

These and other features and advantages of the present invention will become apparent from the following detailed description of the preferred embodiments taken in conjunction with the following drawings.

BRIEF DESCRIPTION OF THE DRAWINGS

FIG. 4 shows a cross-sectional view taken along line 4—4 in FIG. 1; and

FIG. 5 is a perspective view of a cabinet in which a plurality of the containers shown in FIG. 1 may be housed.

DETAILED DESCRIPTION OF THE PREFERRED EMBODIMENT

Figure 1:
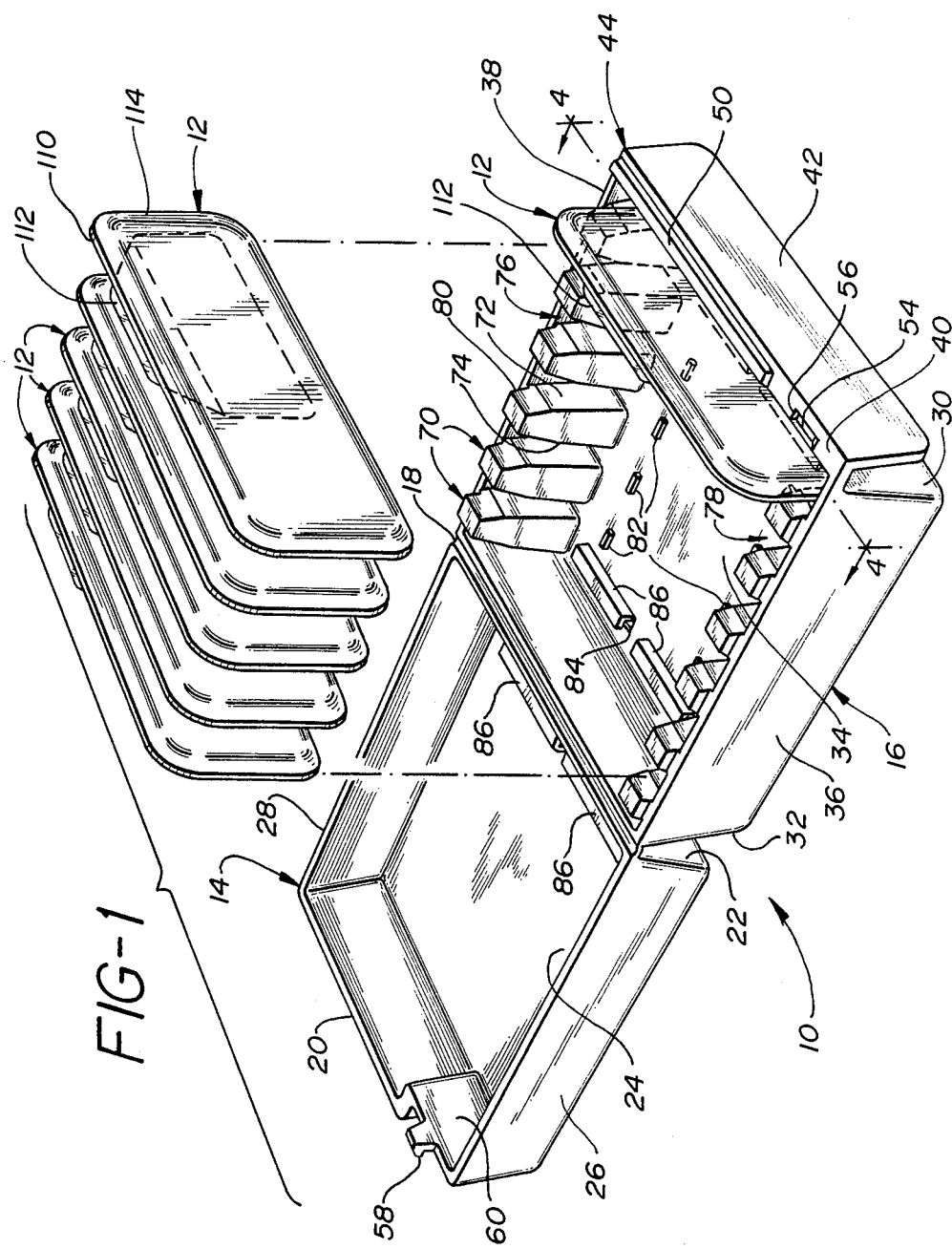
FIG. 1 shows a perspective view of the container of the present invention showing one contact lens package in place and five other contact lens packages in exploded perspective above the container the line for insertion into the container.

Referring now to FIG. 1, there is shown the container 10 of the present invention with six individual packages 12 each containing a contact lens. Package 12 has a molded base 110 with a depression 112 projecting toward one side of molded base 110. The other side of base 110 is opened and covered with an adhesive sealing material 114. Package 12 is intended to hold a soft contact lens which must be kept in a liquid medium, preferably saline solution.

Container 10 has a top portion 14 and a bottom portion 16 preferably made of a suitable molded plastic hinged together along hinge 18 which is preferably molded integrally with top and bottom 14 and 16.

Top 14 has a front wall 20, rear wall 22, top surface 24 and left and right side walls 26 and 28. Bottom 16 has front wall 30, back wall 32, bottom surface 34 and left and right side walls 36 and 38. Hinge 18 is integral with the edge of surface 22 of top 14 and surface 32 of bottom 16.

Figure 2:
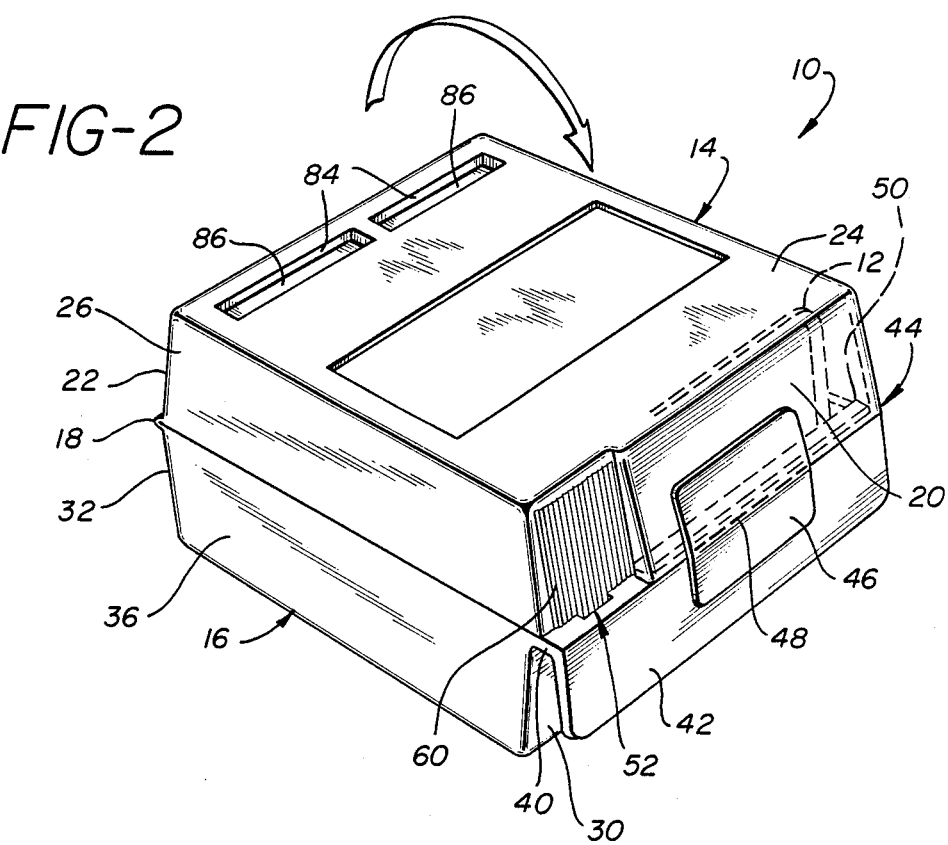
FIG. 2 shows a perspective view of the container in the closed position.

Projecting from front 30 of bottom 16 and extending across the entire upper edge of front 30 is an extension 40 which extends generally parallel to bottom 34 of bottom portion 16. A skirt 42 projects downward from extension 40 and forms an edge 44 with extension 40. As can be seen in FIG. 2, front surface 20 of top 14 mates directly with edge 44 when container 10 is closed and skirt 40 is aligned at the same angle as front surface 20 of top portion 14. Also as shown in FIG. 2, a label 46 is attached to surface 20 and skirt 42 across the seam formed at edge 44 by adhesive or other means. To open container 10 one must tear label 46 along perforated line 48. Label 46 provides the several functions of identifying the contents of container 10, sealing container 10 closed and giving an indication of whether anyone has previously opened or tampered with container 10.

Referring again to FIG. 1, an upstanding ridge 50 extends from the top surface of extension 40 behind the seam along which top 14 and bottom 16 close to inhibit the tampering with individual packages 12 of contact lenses. For example, by inserting a needle through the seam where top and bottom 14 and 16 meet at edge 44. Upstanding ridge 50 extends across extension 40 from one edge all the way to the area where top and bottom 14 and 16 are latched together. Individual packages 12 of contact lenses are aligned so that the portion of package 12 which houses a soft contact lens in a liquid solution is aligned behind upstanding ridge 50 to protect package 12 against puncturing with a needle or other sharp object which could allow the liquid to leak out of package 12. If the liquid leaks out the soft contact lens will dry out and perhaps be destroyed.

Figure 3:
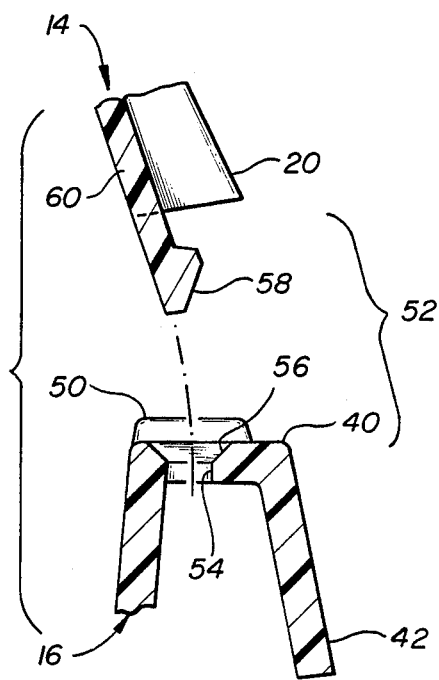
FIG. 3 shows an exploded cross-sectional view of two parts of the latch for the container of FIG. 1.

Referring now to FIG. 3, there is shown an exploded cross-sectional view of the latch 52 used to hold top and bottom 14 and 16 together. Latch 52 includes a slot 65 in extension 40. Slot 54 has a chamfered inlet 56. The other portion of latch 52 is a hooked projection 58 extending from front surface 20 of top 14 and aligned with slot 54. Chamfer 56 guides the point of hooked projection 58 into slot 54. Hooked projection 58 is made of a resilient material which is deflected by chamfer 56 and then springs back so that hooked projection 58 catches on the back of slot 54.

Referring now to FIG. 2, it can be seen that latch 52 is recessed for easier handling. Front wall 20 of top 14 has an offset portion 60 which recesses latch 52 from the rest of front wall 20. The exterior surface of offset 60 may be roughened for better gripping. To open latch 52 a user may conveniently place one's thumb on surface 60 and several fingers on back walls 22 and 32 of top 14 and bottom 16 respectively and extend the fingers across hinge 18. By squeezing offset portion 60 toward rear wall 22, container 10 will easily open.

Referring again to FIG. 1, the details of the interior of container 10 will now be discussed. The number of projections 70 extend upwardly from bottom surface 34 along the inside surfaces of left and right side walls 36 and 38 of bottom portion 16. Each projection 70 is spaced a regular distance away from its adjacent projection 70 and spaced at convenient intervals along the entire left and right sides 36 and 38. The opposing surfaces 72 and 74 of neighboring projections provide a slot 76 into which the corresponding edge of package 12 fits conveniently. Each slot 76 on one side of bottom portion 16 is aligned with a corresponding slot 78 on the opposite side of bottom portion 16. A plurality of packages 12 may be placed in bottom portion 16 and held in position by slots 76 and 78. The top portion 80 of each projection 70 extends up above the upper edge of side walls 36 and 38 of bottom portion 16. This extended upper part 80 of each projection 70 provides a further barrier to protect the individual packages against tampering when container 10 is closed.

Still referring to FIG. 1, container 10 may be used to hold a plurality of packages 12 during steam sterilization. Bottom surface 34 of bottom portion 16 has a number of small steps 82 projecting upwardly from bottom surface 34 and aligned in the middle of slots 76 and 78. When each individual package 12 is placed in container 10 small steps 82 will elevate each package 12 slightly above bottom surface 34 to provide for easy circulation of sterilizing steam.

The bottom surface 34 also includes slots 84 to allow sterilizing steam to circulate through the container and to allow water that may form during condensation after steam sterilization to drain from container 10. Slots 84 are obscured by an L-shaped baffle 86 to minimize tampering and particularly to inhibit the insertion of a sharp instrument which could be used to puncture package 12 and drain the liquid in which the soft contact lenses are stored from package 12.

During sterilization a number of packages 12 are placed in bottom portion 16 of container 10 aligned in slots 76 and 78 and elevated above the bottom surface 34 by steps 82. Container 10 is left open. A large number of open containers 10 can be placed in an autoclave (not shown) and sterilizing steam will circulate throughout the cluster of opened containers 10, particularly through slots 84. When containers 10 are removed from the autoclave, they can be closed and latch 52 will engage to hold top portion 14 and bottom portion 16 together. An identifying label 46 may be placed across edge 44 extending onto front wall 20 and skirt 42. Any water which condenses inside container 10 while it cools can drain through slots 84.

When container 10 is closed and label 46 is attached, container 10 has several tamperproof and tamper evidence features. Upstanding ridge 50 prevents the insertion of a sharp object through label 46 along edge 44. Depressions 112 of packages 12 which hold the contact lens are aligned behind upstanding ridge 50. Even if one succeeds in introducing a sharp object through the front surface of container 10 in the area of latch 52 where upstanding ridge does not extend, one will not succeed in draining the saline solution from package 12 because the depression 112 which forms the liquid reservoir is not exposed to the latch area 52. If one tries to introduce a sharp object through the seams at the sides of the package, the tops 80 of projections 70 protect the reservoir in depressions 112 from the side. Hinge 18 protects the package from the rear. Baffles 86 protect the drain slots 84 in top and bottom portions 14 and 16 against tampering.

Referring now to FIG. 5, there is shown a cabinet 90 which may be suitably mounted in a doctor's office, either on the wall or at some other convenient location. Cabinet 90 is divided preferably into three vertical slots 92, 94 and 96 into which a plurality of containers 10 may be inserted. A cover 98 is placed over a large portion of the front surface of cabinet 90 leaving the bottom container 10 in each slot exposed so that it may be easily remove. Skirt 42 acts like a drawer pull to make it easier for the user to remove each container 10 from its appropriate slot. Below slots 92, 94 and 96 are provided one or more work spaces 102, 104 and 106. Cover 98 is preferably made of a transparent material so that the label of each container may be read through cover 98. Cabinet 90 is shown with three slots and three separate work spaces, but any convenient design could be used.

The present invention has been described in conjunction with the preferred embodiment. Those skilled in the art will appreciate that many modifications and changes may be made in the preferred embodiment without departing from the present invention. It is, therefore, not intended to limit the invention except as set forth in the attached claims.

We claim:

1. A container for a plurality of individually packaged contact lenses for holding said individual packages during sterilization and for later acting as a storage and shipping container for said individual packages, comprising:
   a bottom portion having a bottom, integral left and right side walls extending upwardly from said bottom and integral front and back walls extending upwardly from said bottom and integrally attached to said left and right side walls;
   a plurality of projections extending from said bottom and spaced at predetermined intervals along said left and right side walls and integral with the respective side wall along which they extend, each of said projections spaced from the adjacent projection a predetermined distance to provide a slot therebetween for holding said individual package; each of said slots along said right side wall aligned with a corresponding slot along said left side wall;
   a top portion having a top, having integral left and right side walls extending downwardly from said top and integral front and back walls extending downwardly from said top and integral with said left and right side walls;
   a hinge disposed along an edge of said top portion back wall and disposed along said bottom portion back wall and integral therewith for hinging said top portion and said bottom portion together to permit said top portion to rotate about said hinge from an open position to a closed position to form a closed container for said individual packages; and,
   a plurality of steps projecting from said bottom portion bottom and aligned with said slots defined by said projections disposed along said left and right side walls of said bottom portion for providing a means to elevate said individual packages above said bottom portion bottom to facilitate easy circulation of sterilization medium.

2. The container of claim 1 further including at least one drain slot in said bottom of said bottom portion to permit sterilization medium to circulate throughout said container and to permit condensed sterilization medium to drain from said container after sterilization has been completed.

3. The container of claim 1 further including at least one drain slot in the top of said top portion to permit free circulation of sterilization medium about said container during sterilization and to permit the drainage of sterilization medium from said container after sterilization is finished.

4. The container of claim 1 further including latching means for latching said top portion and said bottom portion together when said container is closed and comprising a slot in said bottom portion, a hooked projection extending from said top portion and aligned with said slot, said slot adapted to receive said hooked projection and to hold said top portion and said bottom portion latched together.

5. The container of claim 1 further including an extension extending from said front wall of said bottom portion in a direction generally parallel to said bottom of said bottom portion and disposed across at least a major portion of said bottom portion front wall, said extension defining an edge; and
   a skirt extending downwardly from said extension along said edge and spaced apart from said bottom portion front wall.

6. The container of claim 5 further including means for latching said top portion and said bottom portion together and comprising a slot in said extension and a resilient hooked projection extending from the front wall of said top portion and aligned with said slot.

7. The container of claim 6 further including a recessed portion in said top portion front wall;
   said hooked projection of said latched means extending from said recessed portion; and
   whereby said latch may be easily handled by the user.

8. The container of claim 1 further including tamper resistant means comprising:
   an extension extending from said bottom portion front wall in a direction generally parallel to said bottom portion bottom and extending along at least a major portion of said bottom portion front wall; said extension defining an edge;
   an upstanding ridge extending across a major portion of said extension and spaced away from said edge; and
   whereby when said top portion closes upon said bottom portion, said top portion front wall will be substantially aligned with said edge and said upstanding ridge will be aligned behind the seam formed by the confronting surfaces of said edge and said top portion front wall to inhibit the insertion of an instrument into said container to tamper with said individual packages.

9. The container of claim 1 wherein said projections further include a top portion extending above the top surfaces of said right and left side walls of said bottom portion; and
   whereby when said top portion and said bottom portion are closed together said top portions of said projections tend to inhibit the insertion of an instrument which could damage said individual packages inside said container.

10. The container of claim 3 wherein said drain slots further include baffles to limit access through said drain slots to the interior of the container when said container is closed.

11. A tamper resistant tamper evident container for a plurality of individual packages of contact lenses comprising:

a bottom portion having a bottom surface;

integral left and right side walls extending upwardly from said bottom surface;

integral front and back walls extending upwardly from said bottom surface and integral with said left and right side walls;

a top portion having a top surface;

integral left and right side walls extending from said top surface;

integral front and back walls extending from said top surface and integral with said left and right side walls;

hinging means integrally connecting said top portion back wall and said bottom portion back wall to permit said top portion to rotate from an open position to a closed position forming an enclosure with said bottom portion;

said bottom portion front wall having an extension extending therefrom in a direction generally parallel to said bottom surface and along a major portion of said bottom portion front wall;

said extension defining an edge;

an upstanding ridge extending along a major portion of said extension and spaced apart from said edge so that when said top portion front wall closes upon said bottom portion front wall said upstanding ridge providing a barrier to the insertion of an instrument which may be used to tamper with the contents of the container; and said bottom portion including a plurality of projections extending upwardly from said bottom surface of said bottom portion and spaced at predetermined intervals along said left and right side walls of said bottom portion and projecting a predetermined distance above the top surface of said left and right side walls of said bottom portion, each of said upstanding projections spaced apart from the neighboring upstanding projection along the respective left or right side wall to provide a slot between said upstanding projections for holding said individual package in place in said container, the portion of each projection which extends above the top of said respective left or right side walls providing a barrier to the insertion of an instrument which could be used to damage said individual package when said top portion is closed upon said bottom portion.

12. The container of claim 11 further including a skirt extending downwardly from said extension along said edge;

a label adhesively affixed to said skirt and to said upper portion front wall across the seam between said upper portion front and said edge when said upper portion is closed upon said bottom portion; and whereby said label will help keep said top and bottom portions closed upon one another and said label will provide evidence of attempts to tamper with said container.

13. The container of claim 11 further including at least one drain slot in each of said top portion, top surface and said bottom portion, bottom surface; and baffles associated with each of said drain slots for limiting access through said slots to the interior of said container when said top portion is closed upon said bottom portion.

14. The container of claim 11 further including latching means for holding said top portion and said bottom portion together when said top portion is closed upon said bottom portion and including a slot in said extension and a resilient hooked projection aligned with cooperatively with said slot for latching said upper portion and said bottom portion together when said upper portion is closed upon said bottom portion.

15. The container of claim 1 further including a skirt extending from said bottom portion front wall

* * * * *